(12) United States Patent
Wang et al.

(10) Patent No.: US 11,318,093 B2
(45) Date of Patent: May 3, 2022

(54) DENTAL TOPICAL ANESTHETIC GEL

(71) Applicant: Pac-Dent, Inc., Brea, CA (US)

(72) Inventors: Daniel Wang, Brea, CA (US); Xiao Yang, La Habra, CA (US); Heng Sun, Chino, CA (US)

( * ) Notice: Subject to any disclaimer, the term of this patent is extended or adjusted under 35 U.S.C. 154(b) by 0 days.

(21) Appl. No.: 16/679,043

(22) Filed: Nov. 8, 2019

(65) Prior Publication Data

US 2021/0137833 A1  May 13, 2021

(51) Int. Cl.
| | |
|---|---|
| *A61K 9/06* | (2006.01) |
| *A61K 31/047* | (2006.01) |
| *A61K 31/352* | (2006.01) |
| *A61K 31/167* | (2006.01) |
| *A61K 31/245* | (2006.01) |
| *A61P 23/02* | (2006.01) |
| *A61K 31/343* | (2006.01) |
| *A61K 31/277* | (2006.01) |
| *A61K 9/107* | (2006.01) |
| *A61M 19/00* | (2006.01) |
| *A61K 31/7048* | (2006.01) |

(52) U.S. Cl.
CPC ............... *A61K 9/06* (2013.01); *A61K 9/107* (2013.01); *A61K 31/047* (2013.01); *A61K 31/167* (2013.01); *A61K 31/245* (2013.01); *A61K 31/277* (2013.01); *A61K 31/343* (2013.01); *A61K 31/352* (2013.01); *A61K 31/7048* (2013.01); *A61M 19/00* (2013.01); *A61P 23/02* (2018.01)

(58) Field of Classification Search
CPC .... A61K 9/06; A61K 31/047; A61K 31/7048; A61K 31/352; A61P 23/02
See application file for complete search history.

(56) References Cited

U.S. PATENT DOCUMENTS

| | | | |
|---|---|---|---|
| 2012/0202891 A1* | 8/2012 | Stinchcomb | A61P 29/00 514/733 |
| 2016/0158299 A1* | 6/2016 | Bohus | A61K 31/05 424/725 |
| 2020/0069604 A1* | 3/2020 | Ghalili | A61K 9/006 |

OTHER PUBLICATIONS

Mirhosseini, F. et al. "Antimicrobial Effect of Different Sizes of Nano Zinc Oxide on Oral Microorganisms" Front Dent. 2019; 16(2): 105-112 (Year: 2019).*

* cited by examiner

*Primary Examiner* — Andrew S Rosenthal

(57) ABSTRACT

The present invention relates to a dental topical anesthetic gel containing a full spectrum blend of active cannabinoids and at least one component including tetracaine, benzocaine, lidocaine, and butamben. Further, the dental topical gel may also contain a chemical penetration enhancer, at least one drug to enhance the effects of cannabinoids, at least one antibacterial agent and at least one antifungal agent. The forms and use of the dental topical anesthetic gel are also disclosed.

20 Claims, 2 Drawing Sheets

FIG. 2

DENTAL TOPICAL ANESTHETIC GEL

BACKGROUND OF THE INVENTION

Field of the Invention

The present invention relates generally to dental topical anesthetic gels, and more specifically to anesthetic gels containing a full spectrum blend of active cannabinoids and at least one component including tetracaine, benzocaine, lidocaine, and butamben, as well as compositions/kits containing such gels and methods of using said gels.

Background Information

Although Cannabis (marijuana) remains classified as a Schedule I drug federally as of 2019, a majority of the states in the Union have adopted either full legalization, partial legalization, or decriminalization. This has allowed the development of various commercial products containing Cannabis or Cannabis extracts. Of note are products containing cannabinoids that act upon the body's endocannabinoid system to affect various pharmacological and physiological mechanisms by signaling through the CB1 and CB2 cannabinoid receptors.

Cannabinoids, within the scope of this invention, refer to various non-synthetic phytocannabinoids found in the Cannabis botanical genus. Although over 200 different cannabinoids have been discovered within the Cannabis plant, only a few have had significant research done on them. Of this latter subgroup, tetrahydrocannabinol (THC), cannabidiol (CBD), cannabinol (CBN), cannabichromene (CBC), and cannabigerol (CBG) stand out for their medical significance. These aforementioned cannabinoids have shown anti-bacterial, anti-inflammatory, antipruritic, and pain-relieving properties in multiple peer-reviewed studies. A brief literature review on the subject matter will be discussed below.

Appendino et al. (J Natural Products (2008) 71 (8):1427-1430) discovered that all five of the aforementioned cannabinoids displayed greater antibacterial activity against a variety of common methicillin-resistant *Staphylococcus aureus* strains (MRSA) than the standard antibiotic treatment for the corresponding strain. Briefly, MRSA refers to strains of the common *Staphylococcus aureus* that have acquired multiple drug resistance through natural selection and horizontal gene transfer. MRSA is the cause of several difficult to treat infections in humans. Although MRSA infections can occur in many areas of the body, it is most commonly localized on the skin.

Petrosino et al. (J Pharm Exptl Thera (2018) 365(3):652-663) found that CBD showed potent anti-inflammatory properties in an in vitro model of allergic contact dermatitis (ACD), a skin inflammatory response that occurs after dermal contact with an allergen, by inhibiting the production of the MCP-2 chemokine and other proinflammatory cytokines, whose job it is to activate immune cells and induce inflammation. Other cannabinoids such as CBG, CBC, and cannabidivarin (CBDV) were also shown to have some anti-inflammatory benefits, but required a much higher concentration dosage and to a lesser extent compared to CBD.

Toth et al. (Molecules (2019) 24(5):918) presented a literature survey on the relationship between the endocannabinoid system and skin. The authors reported that while CBD is commonly known as a CB1 antagonist, it can also act as a context-dependent CB1 agonist. This allows CBD to signal though the endocannabinoid system to maintain skin homeostasis and aid barrier formation and regeneration. CBD was shown in multiple clinical studies in vivo and in vitro to improve skin conditions varying from dry skin to atopic dermatitis such as eczema, psoriasis, and scleroderma.

THC's anti-inflammatory properties have been well documented in the past few decades. It has been shown to lower inflammation by inhibiting the synthesis of PGE-2 and stimulating the synthesis of lipooxygenase. THC's anti-inflammatory potency is reported to be twenty times that of aspirin and twice that of hydrocortisone. (Evans, Planta Med. (1991) 57(7):560-67). However, in contrast to the aforementioned drugs, THC achieves this without any cyclooxygenase (COX) inhibition, which relieves any concerns of potential gastrointestinal ulcers and bleeding.

A meta-study by Russo (Ther Clin Risk Manag (2008) 4(1):245-259) on cannabinoids and pain found that all five of the aforementioned cannabinoids except cannabinol were effective analgesics for both acute and chronic pain with minimal adverse effects. (Id.). Specifically, orally ingested cannabinoids were shown to lower daily pain and reduce acute hyperalgesia in a variety of conditions when compared to the placebo treatment in multiple clinical trials. This is believed to be achieved by stimulation of the CB1 receptor.

Although cannabinoids are lipid-soluble and may be absorbed through the skin, its transdermal absorption is significantly less that of oral ingestion or inhalation. The primary physical barrier to transdermal drug delivery is the stratum corneum, the outermost layer of the skin comprising of about 20 layers of flattened cells. Accordingly, there exists a need to improve upon the topical absorption of cannabinoids in the art. Terpenes are a large and diverse category of significantly odorous organic compounds, which are mainly found in plants. Terpenes such as limonene, linalool, pinene and the like were found to act as chemical penetration enhancers (CPE) for cannabinoids. (Bruni, et al., Molecules (2018) 23(10): 2478 and Chen, et al., Molecules (2016) 21:1709). Terpenes are a good candidate for CPE for their low toxicity and skin irritancy when compared to other commonly used synthetic PEs. It is generally believed that terpenes aid skin penetration by increasing the stratum corneum partitioning of the drug.

Cannabinoids are metabolized within the body by enzymes from the cytochrome P450 (CYP450) family, such as CYP2C9 and CYP3A4. Antibiotics such as Clarithromycin and Erythromycin and certain antifungals from the azole class are inhibitors of said enzymes. The inhibition of these CYP450 enzymes slows down cannabinoid degradation and prolongs its pharmacologically active time. (Zendulka, et al., Curr Drug Metab (2016) 17(3):206-226). This allows for the therapeutic effect of a higher dose at a significantly lower dosage.

Cannabinoids' various therapeutic effects have been extensively documented in the last 20 years. U.S. Pat. No. 9,095,563 (herein incorporated by reference in its entirety) discloses a cannabinoid topical formulation consisting of at least one component selected from the group consisting of capsaicin, benzocaine, lidocaine, camphor, benzoin resin, methylsalicilate, triethanolamine salicylate, hydrocortisone, and salicylic acid.

There exists a need for topical compositions of cannabinoids that take advantage of various pharmacological mechanisms that enhance the delivery, absorption, and therapeutic effects of cannabinoids. The present invention seeks to improve on the prior art by disclosing a novel full-spectrum cannabinoid topical composition consisting of certain chemical penetration enhancers to aid absorption and CYP450 inhibitors to lengthen the active time of cannabinoids within the body.

SUMMARY OF THE INVENTION

The present invention relates to an anesthetic dental gel which exploits a synergistic mechanism by which the unwanted psychoactive effects of Cannabis are modulated, while its therapeutic effects are retained.

In embodiments, a dental topical anesthetic gel containing a full spectrum blend of active cannabinoids and at least one component including tetracaine, benzocaine, lidocaine, and butamben is disclosed, where the component is present in an amount of at least about 10 wt. % combined in the topical gel.

In one aspect, the full spectrum blend includes at least two cannabinoids selected from the group of tetrahydrocannabinol (THC), cannabidiol (CBD), cannabinol (CBN), cannabichromene (CBC), cannabigerol (CBG), cannabivarin (CBV), tetrahydrocannabivarin (THCV) and cannabidivarin (CBDV), and combinations thereof.

In another aspect, the composition further includes a chemical penetration enhancer. In a related aspect, the chemical penetration enhancer contains at least one terpene including alpha-pinene, beta-pinene, limonene, beta-myrcene, beta-caryophyllene, linalool, terpinolene and oximene.

In one aspect, the gel further contains a drug that slows cannabinoids degradation. In a related aspect, the drug includes amiodarone, clarithromycin, diltiazem, erythromycin, fluconazole, isoniazid, itraconazole, ketoconazole, miconazole, ritonavir, verapamil, and combinations thereof.

In another aspect, the gel further includes at least one antibacterial agent, at least one fungal agent or both. In a related aspect, the antibacterial agent includes zinc oxide nanoparticles, silver nanoparticles, plant essential oils, clarithromycin, erythromycin, and combinations thereof. In a further related aspect, the antifungal agent includes fluconazole, itraconazole, ketoconazole, miconazole, and combinations thereof.

In one aspect, the gel is a water-in-oil emulsion, an oil-in-water emulsion, a wax-in-oil base, or an oil-in-wax base. In another aspect, the concentration of tetrahydrocannabinol in the composition is no less than about 0.3 wt. %. In a related aspect, the concentration of said chemical penetration enhancer in the topical gel is no less than about 0.05 wt. %.

In embodiments, a method of preventing or treating gingival or periodontal pathology characterized by inflammation in a subject in need thereof is disclosed including administering an effective amount of a composition comprising a full spectrum blend of active cannabinoids, where the full spectrum work in tandem to produce an interdependently enhancing entourage effect.

In a related aspect, the full spectrum blend comprises at least two cannabinoids including tetrahydrocannabinol (THC), cannabidiol (CBD), cannabinol (CBN), cannabichromene (CBC), cannabigerol (CBG), cannabivarin (CBV), tetrahydrocannabivarin (THCV), cannabidivarin (CBDV), and combinations thereof.

In a further related aspect, the composition further includes a chemical penetration enhancer, where the enhancer increases the absorption and the effect of said cannabinoids.

In another aspect, the composition further includes one or more drugs that slow cannabinoids degradation and enhance the effects of the cannabinoids and lengthens their pharmaceutically active time.

In embodiments, a kit is disclosed including a dental topical anesthetic gel containing a full spectrum blend of active cannabinoids and at least one component including tetracaine, benzocaine, lidocaine, and butamben, where the component is present in an amount of at least about 10 wt. % combined in the topical gel, a container having kit components; and instructions for application of the gel to a subject in need thereof.

BRIEF DESCRIPTION OF THE DRAWINGS

FIG. 2 shows groupings of various components of the endocannabinoid system.

DETAILED DESCRIPTION OF THE INVENTION

Figure 1:
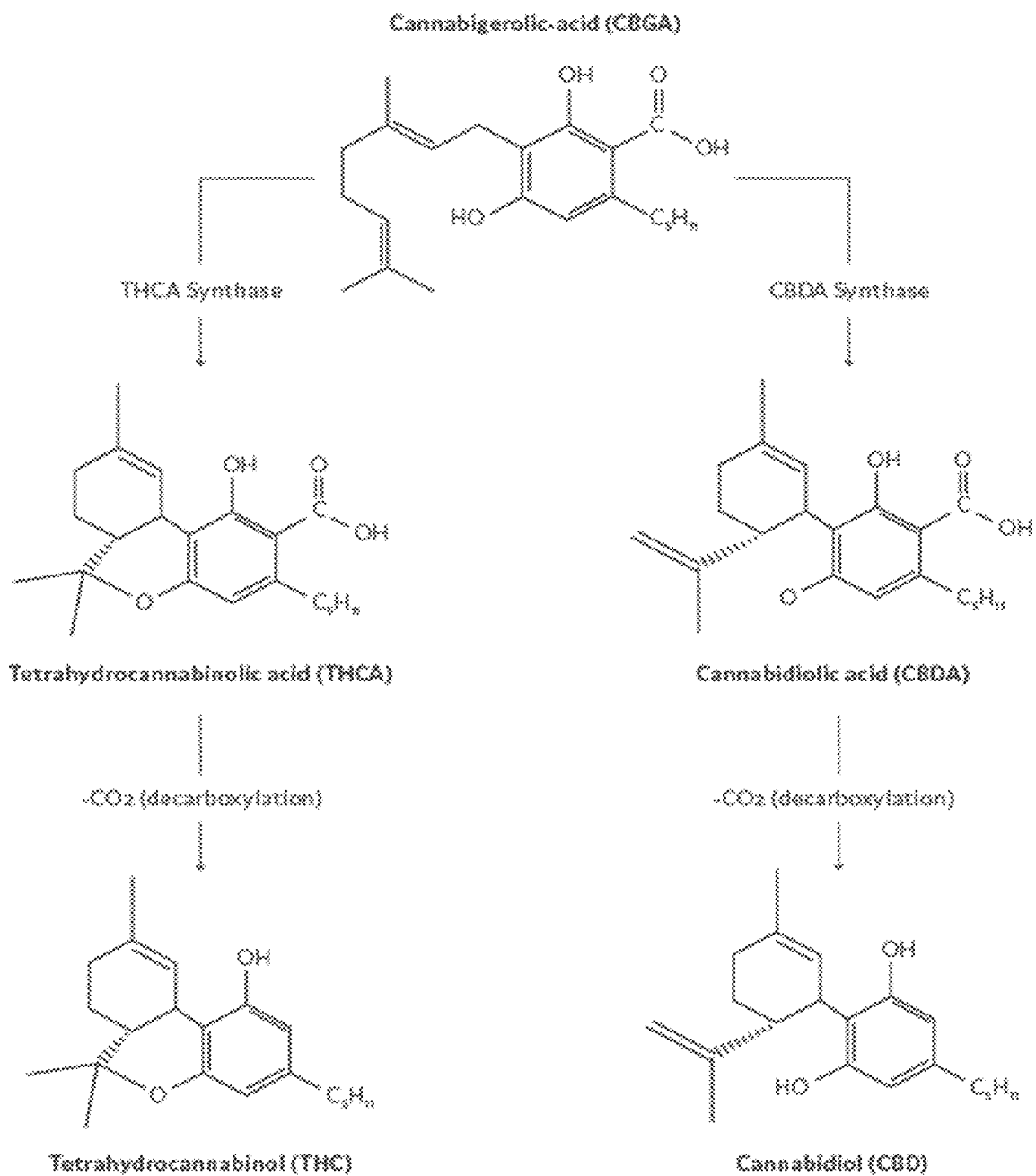
FIG. 1 is a scheme for decarboxylation and synthesis of the two principal cannabinoids, THC and CBD.

Before the present compositions, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "a component" includes one or more components, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein can be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus <10% of a particular term and "substantially" and "significantly" will mean plus or minus >10% of the particular term.

The present invention relates to a dental topical anesthetic composition comprising a full spectrum blend of major cannabinoids and at least one anesthetic agent consisting of tetracaine, benzocaine, lidocaine, and butamben. Furthermore, the invention discloses mechanisms to enhance the delivery, absorption, and therapeutic effects of cannabinoids by the inclusion of various substances that will be detailed below.

Within the scope of the present invention, a full-spectrum cannabinoid topical composition may include a combination of all 8 major cannabinoids: tetrahydrocannabinol (THC), cannabidiol (CBD), cannabinol (CBN), cannabichromene (CBC), cannabigerol (CBG), cannabivarin (CBV), tetrahydrocannabivarin (THCV), and cannabidivarin (CBDV). Although THC has desirable therapeutic benefits, its psychoactive effects are undesirable in a non-recreational environment. However, these adverse side effects can be mitigated by the inclusion of other major cannabinoids, specifically CBD, which can assuage some of the anxiety and forgetfulness produced by THC. Taken together, these cannabinoids work in tandem to create an interdependently enhancing entourage effect. The entourage effect is a synergistic mechanism by which the unwanted psychoactive effects of Cannabis are modulated, while its therapeutic effects are retained. Synthesis and structures of THC and CBD may be seen in FIG. 1.

Figure 2:
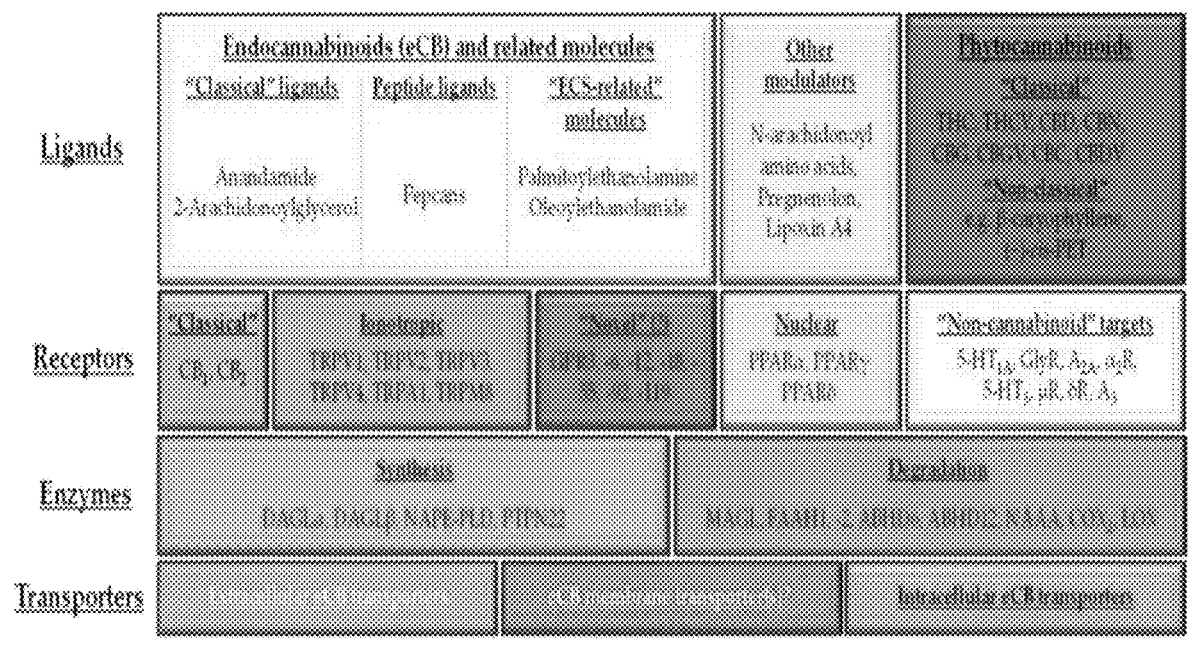

A cannabinoid is one of a class of diverse chemical compounds that acts on cannabinoid receptors, also known as the endocannabinoid system in cells that alter neurotransmitter release in the brain. Components of the endocannabinoid system may be seen in FIG. 2. Ligands for these receptor proteins include the endocannabinoids produced naturally in the body by animals; phytocannabinoids, found in cannabis; and synthetic cannabinoids, manufactured artificially. The most notable cannabinoid is the phytocannabinoid tetrahydrocannabinol (THC), the primary psychoactive compound in cannabis. Cannabidiol (CBD) is another major constituent of the plant.

The endo/phyto-cannabinoids include but are not limited to: N-acylethanolamindes which include N-arachidonoylethanolamide (better known as anandamide or more simply AEA), N-palmitoyl-ethanolamine (PEA), N-linoleoylethanolamide (LEA) and N-oleoylethanolamine (OEA).

Several classes of compounds with similarities in structure and/or activities to the THC purported active ingredient of the marijuana source plant have been identified. These are available in several plants outside the Cannabis genus and can be, cultured (e.g., through selective breeding or genetic engineering), extracted, purified or synthesized chemically de novo or from derivatives. Such compounds include, but are not limited to:

Cannabigerol class: cannabigerolic acid (CBGA) (antibiotic); cannabigerolic acid monomethylether (CBGAM); cannabigerol (CBG) (antibiotic, antifungal, anti-inflammatory, analgesic); Cannabigerol monomethylether (CBGM); cannabigerovarinic acid (CBGVA); Cannabigerovarin (CBGV).

Cannabichromene class: Cannabichromenic acid (CBCA); Cannabichromene (CBC) (antibiotic, antifungal, anti-inflammatory, analgesic); Cannabichromevarinic acid (CBCVA); Cannabichromevarin (CBCV); Cannabidiolic acid (CBDA) (antibiotic); Cannabidiol (CBD) ((antioxidant, anxiolytic, antispasmodic, anti-inflammatory, analgesic); cannabidiol monomethylether (CBDM); cannabidiol C4 (CBD-C4); cannabidivarinic acid (CBDVA); cannabidivarin (CBDV); cannabidiorcol (CBD-C1); $\Delta^9$-tetrahydrocannabinolic acid A (THCA-A); $\Delta^9$-tetrahydrocannabinolic acid B (THCA-B); 6a,10a-trans-6a,7,8,10a-tetrahydro-6,6,9-trimethyl-3-pentyl-6H-dibenzo[b,-d]pyran-1-ol, ($\Delta^9$-tetrahydrocannabino-, THC) (analgesic, antioxidant, antiemetic, anti-inflammation); $\Delta^9$-tetrahydrocannabinolic acid-C4 (THCA-C4); $\Delta^9$-tetrahydrocannabinol-C4 (THC-C4); $\Delta^9$-tetrahydrocannabivarinic acid (THCVA); $\Delta^9$-tetrahydrocannabivarinic (THCV); $\Delta^7$-cis-isotetrahydrocannabivarin; $\Delta^9$-tetrahydro-cannabiorcolic acid (THCA-C1); tetrahydrocanabiorcol (THC-C1).

$\Delta^8$-tetrahydrocannabinol class: $\Delta^8$-tetrahydrocannabinolic acid ($\Delta^8$-TCA); $\Delta^8$-tetrahydrocannabinol ($\Delta^8$-THC).

Cannabicyclol class: cannabicyclol (CBL); cannabicyclolicacid (CBLA); cannabicyclovarin (CBLV).

Cannabieson class: cannabiesoic acid A (CBEA-A); cannabiesoic acid B (CBEA-B); cannabieson (CBE).

Cannabinol and cannabinodiol class: cannabinolic acid (CBNA); cannabinol (CBN); cannabinol methylether (CBNM); cannabinol-C4 (CBN-C4); cannabivarin (CBV); cannabinol-C2 (CBN-C2); cannabiorcol (CBN-C1); cannabinodiol (CBND); cannabinidivarin (CBDV).

Cannabitriol class: cannabitriol (CBT); 10-Ethoxy-9-hydroxy-$\Delta^{6a}$tetrahydrocannabinol (10-EHDT); 8,9-dihydroxy-$\Delta^{6a}$-tetrahydrocannabinol (8,9-DHDT); cannabitriolvarin (CBTV); ethoxy-cannabitriolvarin (CBTVE).

Miscellaneous class: dehydrocannabifuran (DCBF); cannabifuran (CBF); cannabichromanon (CBCN); cannabicitran (CBT); 10-oxo-$\Delta^{6a}$-tetrahydrocannabinol (OTHC); $\Delta^9$-cis-tetrahydrocannabinol (cis-THC); 3,4,5,6-tetrahydro-7-hydroxy-$\alpha$-$\alpha$-2-trimethyl-9-n-propyl-2,6-m-ethano-2H-1-benzoxocin-5-methanol (2H-iso-HHCV); cannabiripsol (CBR); Trihydroxy-$\Delta^9$-tetrahydrocannabinol (triOH-THC).

LEA, PEA and OEA will bind to one or more of the endogenous cannabinoid receptors, but they are also important because they maintain AEA activity through their inhibition of the FAAH enzyme that is responsible for degrading AEA. N-alkylamides exert selective effects on the CB2, and have been shown to exert anti-inflammatory effects similar to AEA. *Echinacea* contains multiple N-alkylamides that have mimetic effects.

Phytoalkanes, another class of chemical compounds found in various plants, also have demonstrated cannabinolic modulation traits, e.g., N-alkanes ranging from $C_9$ to $C_{39}$, 2-methyl-, 3-methyl-, and some dimethyl alkanes are common in spices such as curcumin. The major alkane present in an essential oil obtained by extraction and steam distillation was the N-$C_{29}$ alkane nonacosane (55.8 and 10.7%, respectively). Other abundant alkanes were heptacosane, 2,6-dimethyltetradecane, pentacosane, hexacosane, and hentriacontane. Curcumin reduces liver fibrosis by modulating cannabinoid receptor transmission.

The following list of compounds have been suggested to have cannabinolic activity (i.e., to bind and modulate activity of at least one human cannabinoid receptor): URB597, URB937, AM374, ARN2508, BIA 10-2474, BMS-469908, CAY-10402, JNJ-245, JNJ-1661010, JNJ-28833155, JNJ-40413269, JNJ-42119779, JNJ-42165279, LY-2183240, Cannabidiol, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597 (KDS-4103), URB694, URB937, VER-156084, V-158866, AM3506, AM6701, CAY10435, CAY10499, IDFP, JJKK-048, JNJ-40355003, JNJ-5003, JW618, JW651, JZL184, JZL195, JZP-372A, KML29, MAFP, MJN110, ML30, N-arachidonoyl maleimide, OL-135, OL92, PF-04457845, SA-57, ST4070, URB880, URB937, indomethacin, MK-886, resveratrol, cis-resveratrol, aspirin, COX-1 inhibitor II, loganin, tenidap, SC560, FR 122047 hydrochloride, valeryl salicylate, FR122047 hydrate, ibuprofen, TFAP, 6-methoxy-2-naphthylacetic acid, meloxicam, APHS, etodolac, meloxicam, meloxicam sodium salt, N-(4-acetamidophenyl)indomethacin amide, N-(2-phenylethyl)indomethacin amide, N-(3-pyridyl)indomethacin amide, indomethacin heptylester, SC236, sulinac, sulindac sulfide, pravadoline, naproxen, naproxen sodium salt, meclofenamate sodium, ibupropfen, S-ibuprofen, piroxicam, ketoprofen, S-ketoprofen, R-ibuprofen, ebselen, ETYA, diclofenac, diclofenac diethylamine, flurbiprofen, fexofenadine, pterostilbene, pterocarpus marsupium, 9,12-octadecadiynoic acid, ketorolac (tromethamine salt), NO-indomethacin, S-flurbiprofen, sedanolide, green tea extract (e.g., epicatechin), licofelone, lornoxicam, racibuprofen-d3, ampiroxicam, zaltoprofen, 7-(trifluoromethyl)1H-indole-2,3-dione, aceclofenac, acetylsalicylic acid-d4, S-ibuprofen lysinate, loxoprofen, CAY10589, ZU-6, isoicam, dipyrone, YS121 and MEG (mercaptoethylguanidine) and thus may be appropriate for use in the present invention.

In embodiments, a full spectrum blend of active cannabinoids refers to at least two cannabinoids including, but not limited to, tetrahydrocannabinol (THC), cannabidiol (CBD), cannabinol (CBN), cannabichromene (CBC), cannabigerol (CBG), cannabivarin (CBV), tetrahydrocannabivarin (THCV) and cannabidivarin (CBDV), which may work in tandem to produce an interdependently enhancing entourage effect.

Tetrahydrocannabinol (THC) is the principal psychoactive constituent of cannabis. With chemical name $\Delta^9$-tetrahydrocannabinol, the term THC also refers to cannabinoid isomers. Recent research shows that THC exhibits potent anti-inflammatory and analgesic activity, is neuroprotective, and reduces intraocular pressure, spasticity, and muscle tension.

Cannabidiol (CBD) is a phytocannabinoid discovered in 1940. It is the most common cannabinoid produced by cannabis plants and accounts for up to 40% of the plant's extract. And because of the recent breeding efforts, CBD is becoming more commonly found. CBD exhibits analgesic and anti-inflammatory effects across a wide range of symptoms and conditions. CBD is also a very potent antioxidant. According to recent research, CBD has been shown to eliminate some of THC's unpleasant adverse effects, modulating its psychoactivity and reducing the incidence of THC-induced sedation, anxiety, and rapid heartbeat.

Cannabinol (CBN) is the oxidation byproduct of THC and among the more common cannabinoids found in the cannabis products. Studies on CBN have found that it may be a potent antibacterial agent. CBN may also be a powerful neuroprotectant and a potent anti-inflammatory agent. Further, a recent study indicated that CBN might be useful in treating burns because it reduces perceived thermal sensitivity.

Cannabichromene (CBC) has been shown to block pain and inflammation associated with collagen-induced osteoarthritis. Cannabinoids like CBC act on inflammation differently than non-steroidal anti-inflammatory drugs (NSAIDs), and don't have the side effects of these medications. In another example of the entourage effect, CBC in combination with THC had significant anti-inflammatory response in a recent animal study; together, the two cannabinoids produced a much greater effect on inflammation than by themselves.

CBG is Cannabigerol (CBG) is a non-psychoactive cannabinoid that plays an important role in the biochemistry of the cannabis plant. CBG acts as a chemical precursor to other cannabinoids such as THC and CBD. In animal experiments, CBG was found to be effective in decreasing the inflammation characteristics. European research shows evidence that CBG is an effective antibacterial agent, particularly against methicillin-resistant *Staphylococcus aureus* (MRSA) microbial strains resistant to several classes of drugs.

As disclosed herein, while not being bound by theory, full spectrum blend of these active cannabinoids works in tandem to produce an interdependently enhancing entourage effect. Further, the ratio of the drugs (e.g., tetracaine, benzocaine, lidocaine, and butamben) and cannabinoids allows for over-lapping anesthetic effect and lengthens its pharmaceutically active time. In embodiments, benzocaine may be present at about 1% to about 5%, about 5% to about 10%, about 10% to about 15%, or about 15% to about 20% relative to cannabinoid; lidocaine may be present at about 1% to about 4%, about 4% to about 6% or about 6% to about 8% relative to cannabinoid; tetracaine may be present at about 1% to about 2%, about 2% to about 3%, or about 3% to about 4% relative to cannabinoid. In a related aspect, the benzocaine is present at about 205, lidocaine is present at about 8% and tetracaine is present at about 4% relative to cannabinoid concentration.

The present invention further comprises certain local drugs, chemical penetration enhancers, antibacterial agent and antifungal agents, which will be disclosed in turn.

Certain drugs are incorporated to slow cannabinoids degradation and consequently lead to enhance the effects of cannabinoids and lengthens its pharmaceutically active time. In a related aspect, such drugs include, but are not limited to, amiodarone, clarithromycin, diltiazem, erythromycin, fluconazole, isoniazid, itraconazole, ketoconazole, miconazole, ritonavir, verapamil, and combinations thereof. In embodiments, the drugs may be present at about 0.1% to about 0.5%, about 0.5% to about 1.0%, about 1.0% to about 1.5%, or about 1.5% to about 2.0% w/v. In a related aspect, the drug concentration is about 0.1% to about 2.0% w/v.

Terpene, as a chemical penetration enhancer in the present invention, is selected from the group of alpha-pinene, beta-pinene, limonene, beta-myrcene, beta caryophyllene, linalool, terpinolene, oximene, and combinations thereof. Chemical penetration enhancers are agents that increase the transport of a drug across the skin barrier. They exert their effect by using a range of mechanisms such as disrupting the lipid bilayer structure in the stratum corneum (SC) and thereby increasing the drug's diffusion coefficient, extracting lipids from the SC, altering the solvent nature of the SC and consequently modifying the drug partitioning coefficient, acting on intracellular keratin, and the like. In a related aspect, terpene, as a chemical penetration may be used, which enhancer allows for better absorption of Cannabinoids and therefore provides enhanced anesthetic effect and lengthened pharmaceutically active time of the topical anesthetic gel. In embodiments, the chemical penetration enhancer is about 2% to about 3%, about 3% to about 4%, or about 4% to about 5% w/v. In a related aspect, the enhancer is present at about 2% to about 5% w/v.

Antibacterial agents are a group of materials that fight against pathogenic bacteria. Thus, by killing or reducing the metabolic activity of bacteria, their pathogenic effect in the biological environments will be minimized. Furthermore, these materials can prevent bacterial plaque accumulation in the oral environment and therefore, can reduce the prevalence of plaque-related diseases such as caries. Antibacterial agents are included in the present invention to keep a healthy oral environment. In a related aspect, at least one antibacterial agent includes, but is not limited to, zinc oxide nanoparticles, silver nanoparticles, plant essential oils, clarithromycin, erythromycin, and combinations thereof. In embodiments, the agents may be present at about 0.1% to about 0.5%, about 0.5% to about 1.0%, about 1.0% to about 1.5%, or about 1.5% to about 2.0% w/v. In a related aspect, the drug concentration is about 0.1% to about 2.0% w/v.

An antifungal agent is a drug that selectively eliminates fungal pathogens from a host with minimal toxicity to the host. Antifungal agents are disclosed in the present invention to kill fungi or inhibit their growth for the benefits of the oral environment. In embodiments, at least one antifungal agent is selected from the group consisting of fluconazole, itraconazole, ketoconazole, miconazole, and combinations thereof. In embodiments, the antifungal agent is present at about 0.1% to about 0.2%, about 0.2% to about 0.5%, about 0.5% to about 0.7%, or about 0.7% to about 1.0% w/v.

The disclosed novel compositions are also suitable for formulating for standard oral applications because they can be combined with excipients including, but not limited to, flavorings, preservatives, and other active ingredients, including, but not limited to, nutrients, vitamins, omega-3 fatty acids, hyaluronic acid, disinfectants of the oral cavity, steroidal or non-steroidal anti-inflammatories, wound healing agents, analgesics, and antihistamines.

The composition of the invention may further comprise the usual adjuvants and/or additives such as preservatives/antioxidants, fatty substances/oils, water, organic solvents, silicones, thickeners, softeners, emulsifiers, in addition to antifoaming agents, moisturizers, fragrances, sweeteners, surfactants, fillers, sequestering agents, anionic, cationic, nonionic or amphoteric polymers or mixtures thereof, propellants, acidifying or basifying agents, dyes, colorants, stabilizers, whitening agents, antibacterial agents, preservative active ingredients or any other ingredients usually formulated into drugs. The additives and/or additional active ingredients can, based on the desired product, easily be chosen by a person skilled in the art.

Physiologically acceptable carriers or excipients for use with the inventive pharmaceutical compositions can be routinely selected for a particular use by those skilled in the art. These include, but are not limited to, solvents, buffering agents, inert diluents or fillers, suspending agents, dispersing or wetting agents, preservatives, stabilizers, chelating agents, emulsifying agents, anti-foaming agents, gel-forming agents, ointment bases, humectants, emollients, and skin protecting agents.

Examples of solvents are water, alcohols, vegetable, marine and mineral oils, polyethylene glycols, propylene glycols, glycerol, and liquid polyalkylsiloxanes. Inert diluents or fillers may be sucrose, sorbitol, sugar, mannitol, microcrystalline cellulose, starches, calcium carbonate, sodium chloride, lactose, calcium phosphate, calcium sulfate, or sodium phosphate. Examples of buffering agents include citric acid, acetic acid, lactic acid, hydrogenophosphoric acid, and diethylamine. Suitable suspending agents are, for example, naturally occurring gums (e.g., acacia, arabic, xanthan, and tragacanth gum), celluloses (e.g., carboxymethyl-, hydroxyethyl-, hydroxypropyl-, and hydroxypropylmethyl-cellulose), alginates and chitosans. Examples of dispersing or wetting agents are naturally occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a gel composition of the invention to prevent microbial contamination that can affect the stability of the formulation and cause infection in the patient. Suitable examples of preservatives include parabens (such as methyl, ethyl, propyl, p-hydroxybenzoate, butyl, isobutyl, and isopropylparaben), potassium sorbate, sorbic acid, benzoic acid, methyl benzoate, phenoxyethanol, bronopol, bronidox, MDM hydantoin, iodopropynyl butylcarbamate, benzalconium chloride, cetrimide, and benzylalcohol. Examples of chelating agents include sodium EDTA and citric acid.

Examples of emulsifying agents are naturally occurring gums, naturally occurring phosphatides (e.g., soybean lecithin; sorbitan mono-oleate derivatives), sorbitan esters, monoglycerides, fatty alcohols, and fatty acid esters (e.g., triglycerides of fatty acids). Anti-foaming agents usually facilitate manufacture, they dissipate foam by destabilizing the air-liquid interface and allow liquid to drain away from air pockets. Examples of anti-foaming agents include simethicone, dimethicone, ethanol, and ether.

Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carrageenans, hyaluronates, and alginates. Ointment bases suitable for use in the compositions of the present invention may be hydrophobic or hydrophilic, and include paraffin, lanolin, liquid polyalkylsiloxanes, cetanol, cetyl palmitate, vegetable oils, sorbitan esters of fatty acids, polyethylene glycols, and condensation products between sorbitan esters of fatty acids, ethylene oxide (e.g., polyoxyethylene sorbitan monooleate), and polysorbates.

Examples of humectants are ethanol, isopropanol glycerin, propylene glycol, sorbitol, lactic acid, and urea. Suitable emollients include cholesterol and glycerol.

The gel compositions of the invention may, alternatively or additionally, comprise other types of excipients including, thickening agents and bioadhesive polymers.

Thickening agents are generally used to increase viscosity and improve bioadhesive properties of pharmaceutical compositions. Examples of thickening agents include, but are not limited to, celluloses, polyethylene glycol, polyethylene oxide, naturally occurring gums, gelatin, karaya, pectin, alginic acid, and povidone. Particularly interesting are thickening agents with thixotropic properties (i.e., agents whose viscosity is decreased by shaking or stirring). The presence of such an agent in a gel composition allows the viscosity of the composition to be reduced at the time of administration to facilitate its application to the site of interest (e.g., to the gingiva or periodontal pocket) and, to increase after application so that the composition remains at the site of administration.

The following examples will further describe the present invention without, however, at the same time, constituting any limitation thereof.

EXAMPLES

Example 1. Dental Topical Gel with Cannabinoids

A dental topical gel is prepared by mixing a topical formulation with cannabinoids selected from the group of THC, CBD, CBN, CBC, CBG, CBV, THCV and CBDV. The topical formulation consists of at least one component selected from the group consisting of tetracaine, benzocaine, lidocaine, and butamben.

Example 2. Dental Topical Gel for Clear Aligner Users

A dental topical gel is prepared by dispersing cannabinoids in emulsion base for clear aligner users. The topical gel may be applied by painting with a brush a thin layer onto the tooth surface prior to putting on orthodontic aligner or dispensing directly to the space inside orthodontic aligner prior to wearing the aligner.

Example 3. Dental Topical Gel for Orthodontics Patients

A dental topical gel is prepared as Example 2. The topical gel may be applied by painting with a brush a thin layer onto the tooth surface as a supplement to orthodontics treatment.

Example 4. Dental Topical Gel for Mouth Ulcers

A dental topical gel is prepared as Example 2. The topical gel may be applied directly on or around an oral or intraoral ulcer such as a cold or canker sore to alleviate pain and to promote healing of the wound.

Example 5. Dental Topical Gel for Conventional Periodontal Treatment

A dental topical gel is prepared as Example 2. The topical gel may be applied by painting with a brush a thin layer onto the gingival before and after periodontal treatment such as scaling and root planing for anti-bacterial protection, anesthesia, anti-inflammation, and wound healing promotion.

Example 6. Dental Topical Gel for Endodontic Treatment

A dental topical gel is prepared as Example 2. The topical gel may be applied by painting with a brush a thin layer onto the gingival before and after endodontic treatment such as root canal and crowning for anti-bacterial protection, anesthesia, anti-inflammation, and wound healing promotion.

Example 7. Dental Topical Gel for Temporomandibular Joint Syndrome (TMJ)

A dental topical gel is prepared as Example 2. The topical gel may be applied by rubbing and massaging the gel into the parotideo-masseteric fascia to alleviate the pains and inflammation associated with TMJ.

While a number of preferred embodiments of the invention and variations thereof have been described in detail, other modifications and methods of using and applications for the same will be apparent to those of skill in the art. Accordingly, it should be understood that various applications, modifications, materials, and substitutions may be made of equivalents without departing from the spirit of the invention or the scope of the claims. It should be understood that the invention is not limited to the embodiments set forth herein for purposes of exemplification, but is to be defined only by a fair reading of the appended claims, including the full range of equivalency to which each element thereof is entitled. All references recited herein are incorporated by reference herein in their entireties.

We claim:

1. A dental topical anesthetic gel containing a full spectrum blend of active cannabinoids and at least one component selected from the group consisting of tetracaine, benzocaine, lidocaine, and butamben, wherein the component is present in an amount of at least about 10 wt. % combined in the topical gel, wherein at least one cannabinoid is tetrahydrocannabinol (THC), and wherein the concentration of tetrahydrocannabinol is no less than 0.3 wt. %.

2. The dental topical anesthetic gel of claim 1, wherein said full spectrum blend comprises at least two cannabinoids selected from the group consisting of tetrahydrocannabinol (THC), cannabidiol (CBD), cannabinol (CBN), cannabichromene (CBC), cannabigerol (CBG), cannabivarin (CBV), tetrahydrocannabivarin (THCV), cannabidivarin (CBDV), and combinations thereof.

3. The dental topical anesthetic gel of claim 1, further comprising a chemical penetration enhancer.

4. The dental topical anesthetic gel of claim 3, wherein said chemical penetration enhancer comprises at least one terpene selected from the group consisting of alpha-pinene, beta-pinene, limonene, beta-myrcene, beta-caryophyllene, linalool, terpinolene and oximene.

5. The dental topical anesthetic gel of claim 1, further comprising a drug that slows cannabinoid degradation.

6. The dental topical anesthetic gel of claim 5, wherein the drug is selected from the group consisting of amiodarone, clarithromycin, diltiazem, erythromycin, fluconazole, isoniazid, itraconazole, ketoconazole, miconazole, ritonavir, verapamil, and combinations thereof.

7. The dental topical anesthetic gel of claim 1, further comprising at least one antibacterial agent, at least one fungal agent or both.

8. The dental topical anesthetic gel of claim 7, wherein said antibacterial agent is selected from the group consisting of zinc oxide nanoparticles, silver nanoparticles, plant essential oils, clarithromycin, erythromycin, and combinations thereof.

9. The dental topical anesthetic gel of claim 7, wherein said antifungal agent is selected from the group consisting of fluconazole, itraconazole, ketoconazole, miconazole, and combinations thereof.

10. The dental topical anesthetic gel of claim 1, wherein the gel is a water-in-oil emulsion, an oil-in-water emulsion, a wax-in-oil base, or an oil-in-wax base.

11. The dental topical anesthetic gel of claim 3, wherein the concentration of said chemical penetration enhancer in the topical gel is no less than about 0.05 wt. % in the topical gel.

12. A method of preventing or treating gingival or periodontal pathology characterized by inflammation in a subject in need thereof comprising administering an effective amount of the composition of claim 1 comprising a full spectrum blend of active cannabinoids, wherein said full spectrum works in tandem to produce an interdependently enhancing entourage effect.

13. The method of claim 12, wherein said full spectrum blend comprises at least two cannabinoids selected from the group consisting of tetrahydrocannabinol (THC), cannabidiol (CBD), cannabinol (CBN), cannabichromene (CBC), cannabigerol (CBG), cannabivarin (CBV), tetrahydrocannabivarin (THCV), cannabidivarin (CBDV), and combinations thereof.

14. The method of claim 12, wherein the composition further comprises a chemical penetration enhancer, wherein said enhancer increases the absorption and the effect of said cannabinoids.

15. The method of claim 12, wherein the composition further comprises one or more drugs that slow cannabinoid degradation and enhance the effects of said cannabinoids and lengthens their pharmaceutically active time.

16. The method of claim 15, wherein the drug is selected from the group consisting of amiodarone, clarithromycin, diltiazem, erythromycin, fluconazole, isoniazid, itraconazole, ketoconazole, miconazole, ritonavir, verapamil, and combinations thereof.

17. A kit comprising:
   a) dental topical anesthetic gel containing a full spectrum blend of active cannabinoids and at least one component selected from the group consisting of tetracaine, benzocaine, lidocaine, and butamben, wherein the component is present in an amount of at least about 10 wt. % combined in the topical gel, wherein at least one cannabinoid is tetrahydrocannabinol (THC), and wherein the concentration of tetrahydrocannabinol is no less than 0.3 wt. %;
b) a container comprising kit components; and
c) instructions for application of said gel to a subject in need thereof.

18. The kit of claim 17, wherein said full spectrum blend comprises at least two cannabinoids selected from the group of tetrahydrocannabinol (THC), cannabidiol (CBD), cannabinol (CBN), cannabichromene (CBC), cannabigerol (CBG), cannabivarin (CBV), tetrahydrocannabivarin (THCV), cannabidivarin (CBDV), and combinations thereof.

19. The kit of claim 17, further comprising a chemical penetration enhancer.

20. The kit of claim 19, wherein said chemical penetration enhancer comprises at least one terpene selected from the group consisting of alpha-pinene, beta-pinene, limonene, beta-myrcene, beta caryophyllene, linalool, terpinolene and oximene.

* * * * *